United States Patent
Carrick et al.

[11] Patent Number: 5,955,000
[45] Date of Patent: Sep. 21, 1999

[54] CHIRAL COMPOUNDS

[75] Inventors: Benjamin Ross Carrick; John William Goodby; Kenneth Johnson Toyne; Michael Hird, all of Hull; Damien Gerard McDonnell, Malvern, all of United Kingdom

[73] Assignee: The Secretary of State for Defence, United Kingdom

[21] Appl. No.: 08/913,912

[22] PCT Filed: Mar. 28, 1996

[86] PCT No.: PCT/GB96/00742

§ 371 Date: Sep. 25, 1997

§ 102(e) Date: Sep. 25, 1997

[87] PCT Pub. No.: WO96/30462

PCT Pub. Date: Oct. 3, 1996

[30] Foreign Application Priority Data

Mar. 28, 1995 [GB] United Kingdom .................. 9506308

[51] Int. Cl.$^6$ .......................... C09K 19/12; C07C 255/07
[52] U.S. Cl. ................. 252/299.65; 252/299.01; 252/299.61; 252/299.63; 558/402; 558/403
[58] Field of Search .................... 558/406, 402, 558/403; 430/20; 252/299.01, 299.61, 299.65

[56] References Cited

FOREIGN PATENT DOCUMENTS

| A 0 313 235 | 4/1989 | European Pat. Off. . |
| WO 87/05018 | 8/1987 | WIPO . |
| WO A 87 07890 | 12/1987 | WIPO . |

OTHER PUBLICATIONS

Chemical Abstracts, vol. 118, No. 17, Apr. 26, 1993 Columbus, Ohio, US; abstract No. 168830z, T. Kusumoto et al.: "preparation of optically active cyano–containing benzoate compounds as liquid crystal compositions" p. 851: XP002008390 see abstract & JP,A,04 211 043 (Dainippon Ink and Chemicals) Aug. 3, 1992.
Tetrahedron Letters, vol. 36, No. 7, 1995, pp. 1071–1074, XP002008389 T. Kusumoto et al.: "anti–selective alkylation of carboxylate enolates with 2–sulfonyloxyalkanes: a new route to 2–sulfonyloxyalkanes; a new route to optically active 2–arylalkanoic acids" see p. 107, line 11 –line 21.
Database WPI Week 9141 Derwent Publications Ltd., London, GB; AN 91–300262 XP002008391 & JP,A,03 200 755 (Dainippon Ink; Sagami see p. 361 & Chemical Research Center) see p. 361 & Chemical Abstracts, vol. 116, No. 14, Apr. 6, 1992 Columbus, Ohio, US; abstract No. 140767, Takehara et al: "optically active compounds for liquid crystal compositions for display devices" see p. 799; see abstract.

*Primary Examiner*—Johann Richter
*Assistant Examiner*—Ebenezer Sackey
*Attorney, Agent, or Firm*—Nixon & Vanderhye

[57] ABSTRACT

This invention describes compounds of formula (I)

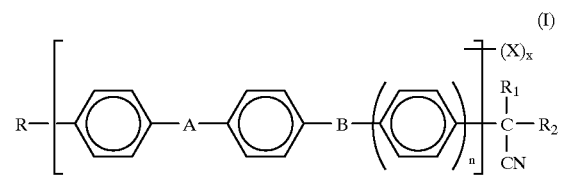

wherein R is $C_{1-16}$ alkyl or alkoxy; X is selected from F and Cl and indicates that one or more of the phenyl rings may be laterally substituted; x is selected from 0–3; A and B are independently selected from $CO_2$, OCO, $\equiv C$ and single bond; $R_1$ and $R_2$ are independently selected from H and $C_{1-16}$ alkyl provided that $R_1$ and $R_2$ are different; n is 0 or 1 provided that if n is zero then B is single bond. These compounds may be used as dopants suitable for use in ferroelectric liquid crystal mixtures.

10 Claims, 7 Drawing Sheets

CHIRAL COMPOUNDS

This invention relates to chiral compounds suitable for use in liquid crystal mixtures and their inclusion in liquid crystal devices.

Liquid crystals can exist in various phases. In essence there are three different classes of liquid crystalline material, each possessing a characteristic molecular arrangement. These classes are nematic, cholesteric and smectic. A wide range of smectic phases exists, for example smectic A and smectic C. Some liquid crystal materials possess a number of liquid crystal phases on varying the temperature, others have just one phase. For example, a liquid crystal material may show the following phases on being cooled from the isotropic phase:—isotropic—nematic—smectic A—smectic C—solid. If a material is described as being smectic A then it means that the material possesses a smectic A phase over a useful working temperature range.

Ferroelectric smectic liquid crystal materials, which can be produced by mixing an achiral host and a chiral dopant, use the ferroelectric properties of the tilted chiral smectic C, F, G, H, I, J and K phases. The chiral smectic C phase is denoted $S_C^*$ with the asterisk denoting chirality. The $S_C$ phase is generally considered to be the most useful as it is the least viscous. Ferroelectric smectic liquid crystal materials should ideally possess the following characteristics: low viscosity, controllable spontaneous polarisation (Ps) and an $S_C$ phase that persists over a broad temperature range, which should include ambient temperature and exhibits chemical and photochemical stability. Materials which possess these characteristics offer the prospect of very fast switching liquid crystal containing devices. Some applications of ferroelectric liquid crystals are described by J. S. Patel and J. W. Goodby in Opt. Eng., 1987, 26, 273.

In ferroelectric liquid crystal devices the molecules switch between different alignment directions depending on the polarity of an applied electric field. These devices can be arranged to exhibit bistability where the molecules tend to remain in one of two states until switched to the other switched state. Such devices are termed surface stabilised ferroelectric devices, e.g. as described in U.S. Pat. No. 5,061,047 and U.S. Pat. No. 4,367,924 and U.S. Pat. No. 4,563,059. This bistability allows the multiplex addressing of quite large and complex devices.

One common multiplex display has display elements, ie pixels, arranged in an x, y matrix format for the display of e.g., alpha numeric characters. The matrix format is provided by forming the electrodes on one slide as a series of column electrodes, and the electrodes on the other slide as a series of row electrodes. The intersections between each column and row form addressable elements or pixels. Other matrix layouts are known, e.g. seven bar numeric displays.

There are many different multiplex addressing schemes. A common feature involves the application of a voltage, called a strobe voltage to each row or line in sequence. Coincidentally with the strobe applied at each row, appropriate voltages, called data voltages, are applied to all column electrodes. The differences between the different schemes lies in the shape of the strobe and data voltage waveforms.

Other addressing schemes are described in GB-2,146,473-A; GB-2,173,336-A; GB-2,173,337-A: GB-2,173,629-A; WO 89/05025; Harada et al 1985 S.I.D. Paper 8.4 pp 131–134; Lagerwall et al 1985 I.D.R.C pp 213–221 and P Maltese et al in Proc 1988 IDRC p 90–101 Fast Addressing for Ferro Electric LC Display Panels.

The material may be switched between its two states by two strobe pulses of opposite sign, in conjunction with a data waveform. Alternatively, a blanking pulse may be used to switch the material into one of its states. Periodically the sign of the blanking and the strobe pulses may be alternated to maintain a net d.c. value.

These blanking pulses are normally greater in amplitude and length of application than the strobe pulses so that the material switches irrespective of which of the two data waveforms is applied to any one intersection. Blanking pulses may be applied on a line by line basis ahead of the strobe, or the whole display may be blanked at one time, or a group of lines may be simultaneously blanked.

It is well known in the field of ferroelectric liquid crystal device technology that in order to achieve the highest performance from devices, it is important to use mixtures of compounds which give materials possessing the most suitable ferroelectric smectic characteristics for particular types of device.

Devices can be assessed for speed by consideration of the response time vs pulse voltage curve. This relationship may show a minimum in the switching time ($t_{min}$) at a particular applied voltage ($V_{min}$). At voltages higher or lower than $V_{min}$ the switching time is longer than $t_{min}$. It is well understood that devices having such a minimum in their response time vs voltage curve can be multiplex driven at high duty ratio with higher contrast than other ferroelectric liquid crystal devices. It is preferred that the said minimum in the response time vs voltage curve should occur at low applied voltage and at short pulse length respectively to allow the device to be driven using a low voltage source and fast frame address refresh rate.

Typical known materials (where materials are a mixture of compounds having suitable liquid crystal characteristics) which do not allow such a minimum when included in a ferroelectric device include the commercially available materials known as SCE13 and ZLI-3654 (both supplied by Merck UK Ltd, Poole, Dorset). A device which does show such a minimum may be constructed according to PCT GB 88/01004 and utilising materials such as e.g. commercially available SCE8 (Merck UK Ltd.). Other examples of prior art materials are exemplified by PCT/GB/86/00040, PCT/GB87/00441 and UK 2232416B.

For all the above applications it is not usual for a single compound to exhibit all of the properties highlighted, for example ferroelectric smectic liquid crystal materials generally consist of a mixture of compounds which when mixed together induce a chiral tilted smectic phase. Chiral dopants are added to a liquid crystalline mixture in order to induce the smectic mixture to become chiral smectic and to induce a Ps in the material, or if the material already possesses a Ps then the introduction of a chiral dopant should result in a change of value for Ps.

Ferroelectric liquid crystal materials are claimed in European Patent Application EP 0313 235 A2.

Most liquid crystal devices incorporate a mixture of materials selected to give desired operating characteristics. The present invention provides liquid crystal materials suitable for incorporating in a wide variety of mixtures to provide the desired characteristics suitable for use in a number of devices.

According to this invention there are provided compounds having a general Formula I:

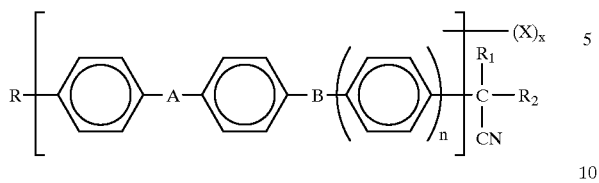

wherein R is $C_{1-16}$ alkyl or alkoxy;

X is selected from F and Cl and indicates that one or more of the phenyl rings may be laterally substituted x is selected from 0–3;

A and B are independently selected from $CO_2$, OCO, C=C and single bond $R_1$ and $R_2$ are independently selected from H and $C_{1-16}$ alkyl provided that $R_1$ and $R_2$ are different;

n is 0 or 1 provided that if n is zero then B is single bond.

Preferably X is F;

Preferably A and B are selected from $CO_2$, OCO and single bond;

Preferably X is F and x is 1 or 2;

Preferably n is 1.

Compounds of Formula I can be included in a material, the material being a mixture of compounds.

The materials of this aspect of the invention may be used in many of the known forms of liquid crystal display devices, for example chiral smectic electrooptic devices. Such a device may comprise a layer of liquid crystal material contained between two spaced cell walls bearing electrode structures and surface treated to align liquid crystal material molecules. The liquid crystal mixtures may have many applications including in ferroelectric devices.

The position and structure of the chiral centre enables such materials to be used as dopants for ferroelectric mixtures, in which the magnitude of spontaneous polarisation can be adjusted to be optimal for use in different types of ferroelectric devices.

The invention will now be described by way of example only with reference to the accompanying drawings of which:

Figure 1:
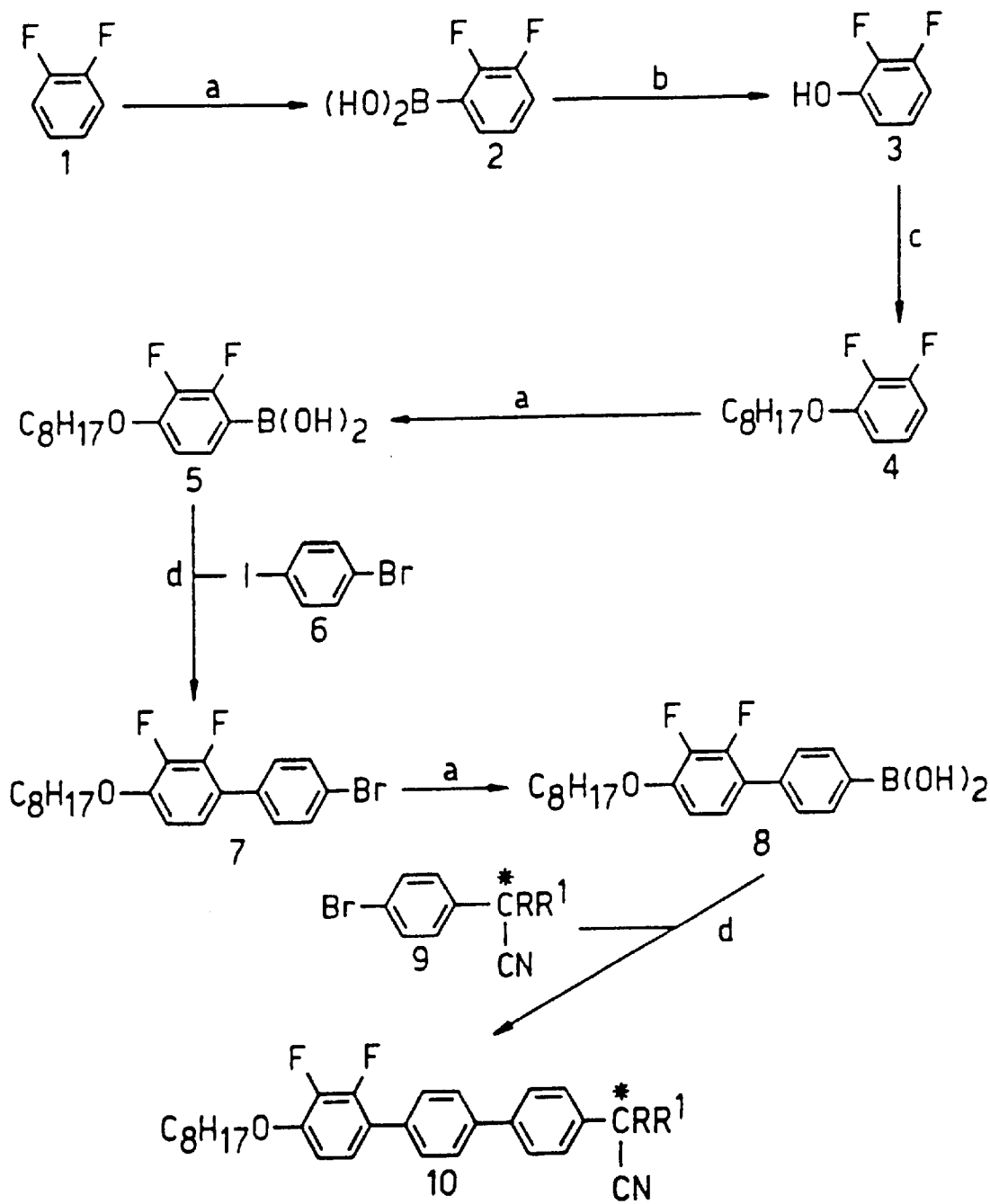
FIGS. 1–9 illustrate synthetic schemes for the synthesis of compounds.
Figure 2:
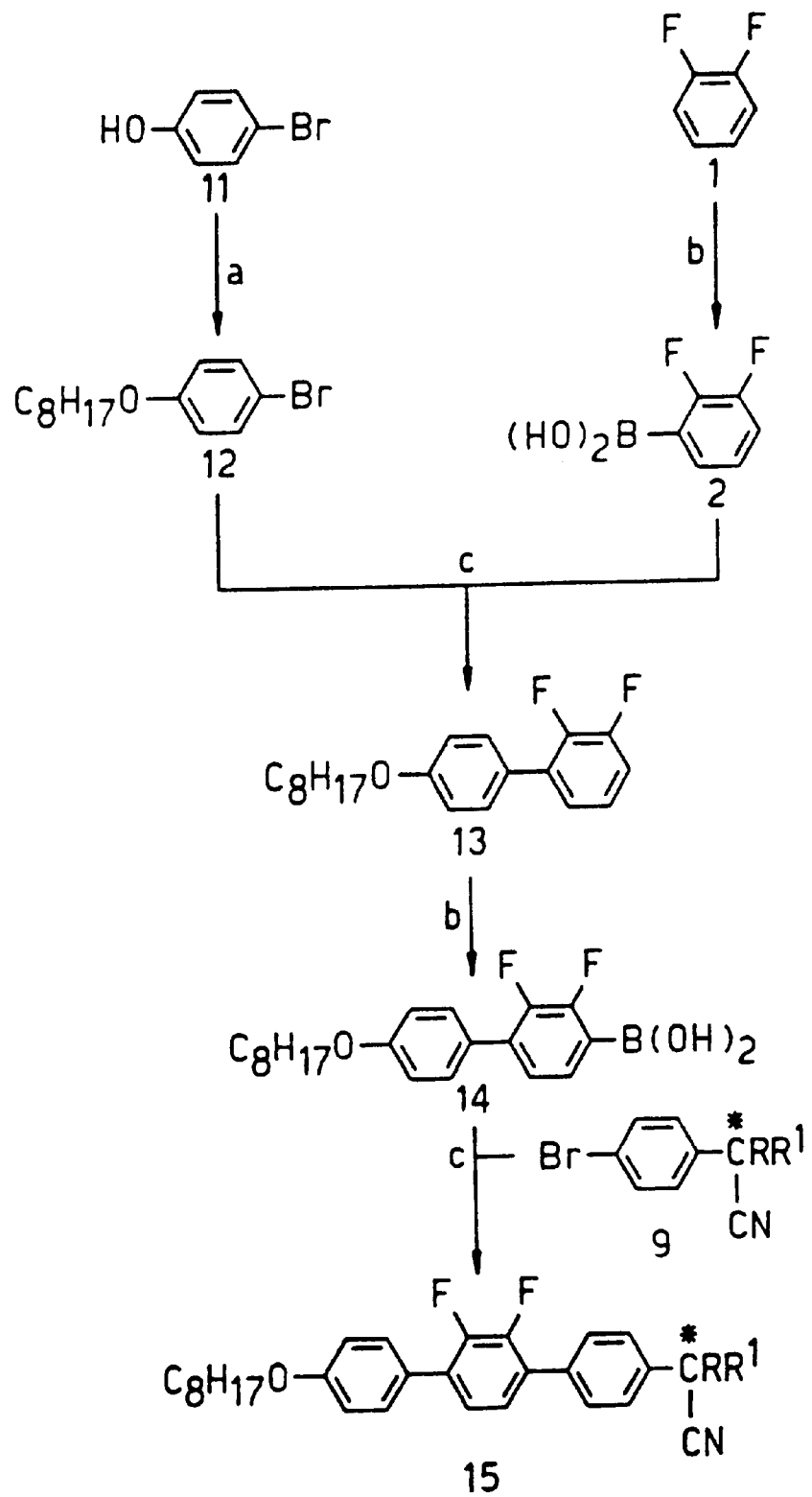
Figure 3:
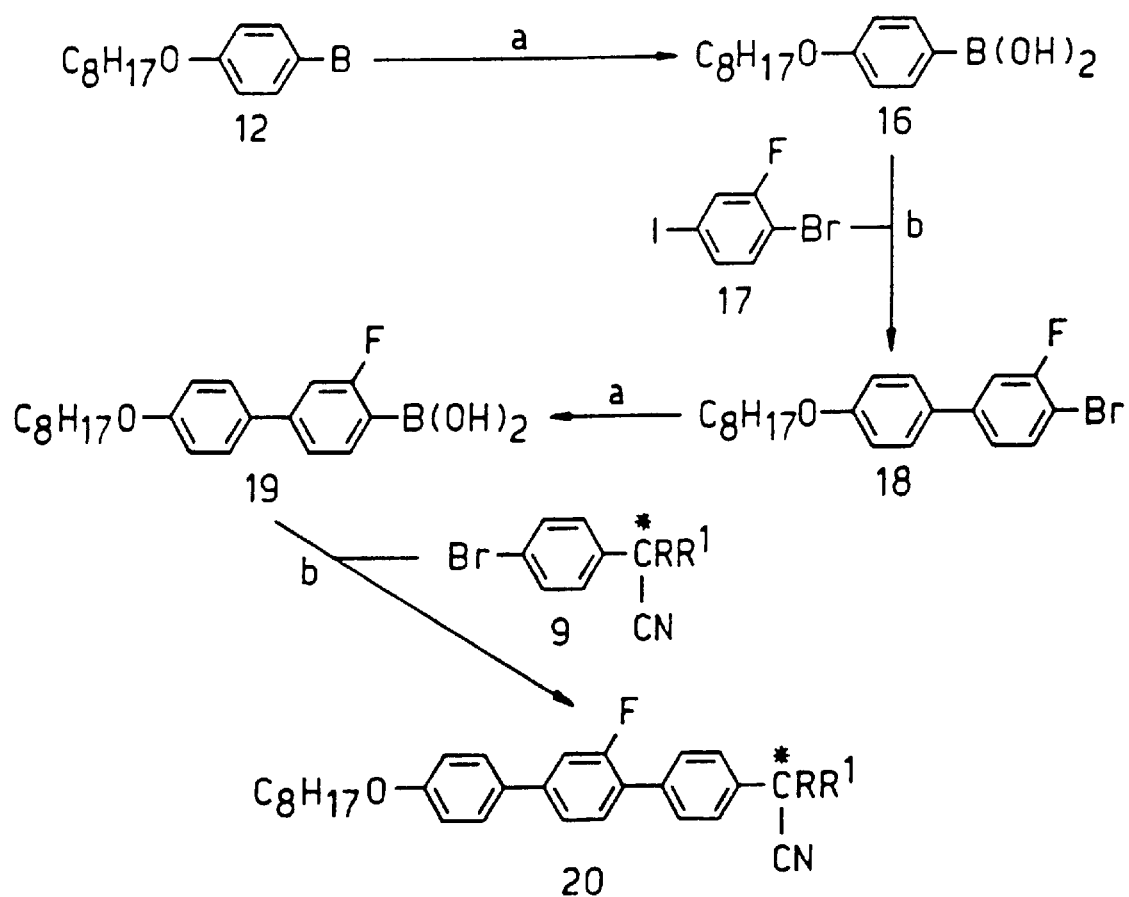
Figure 4:
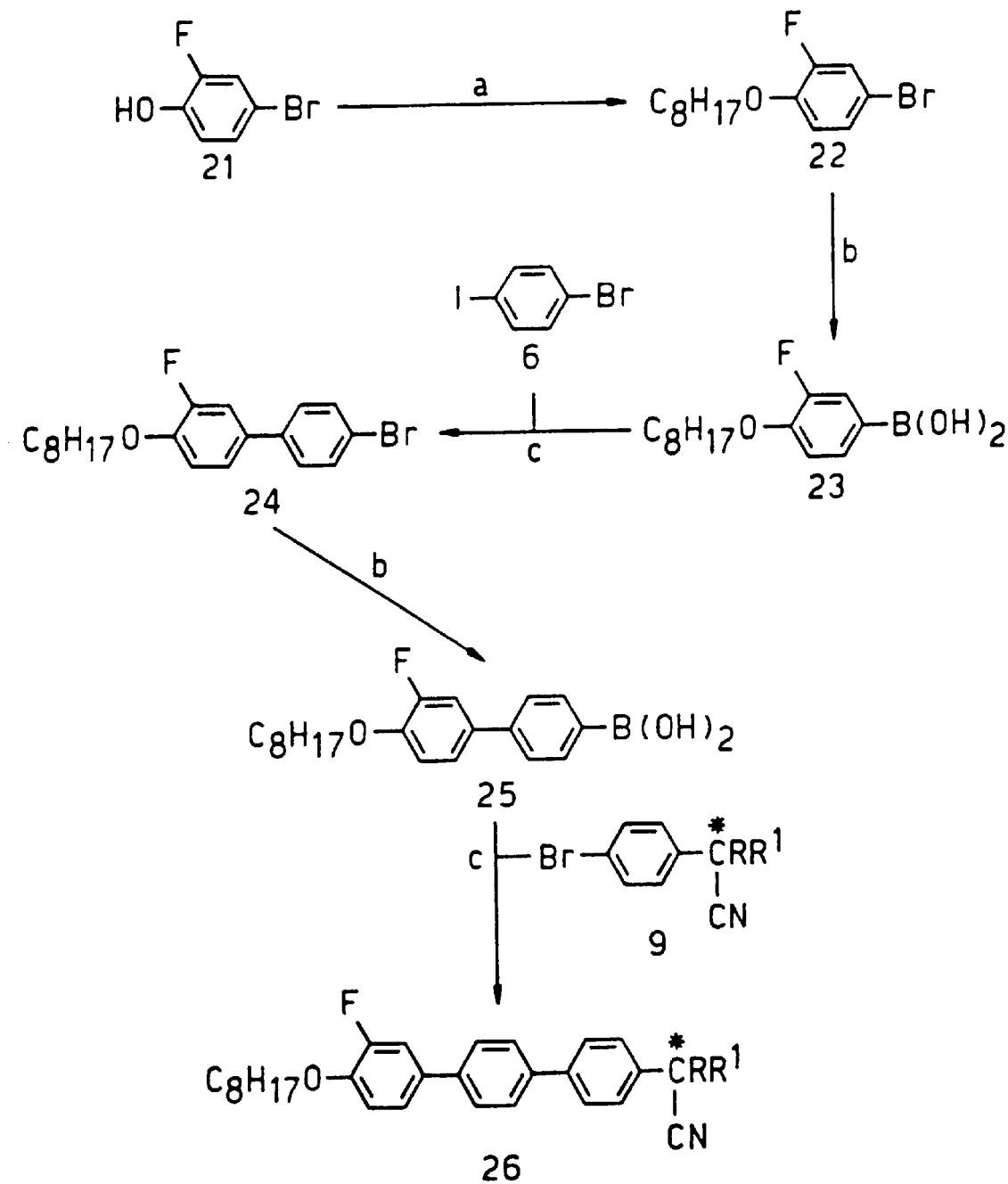
Figure 5:
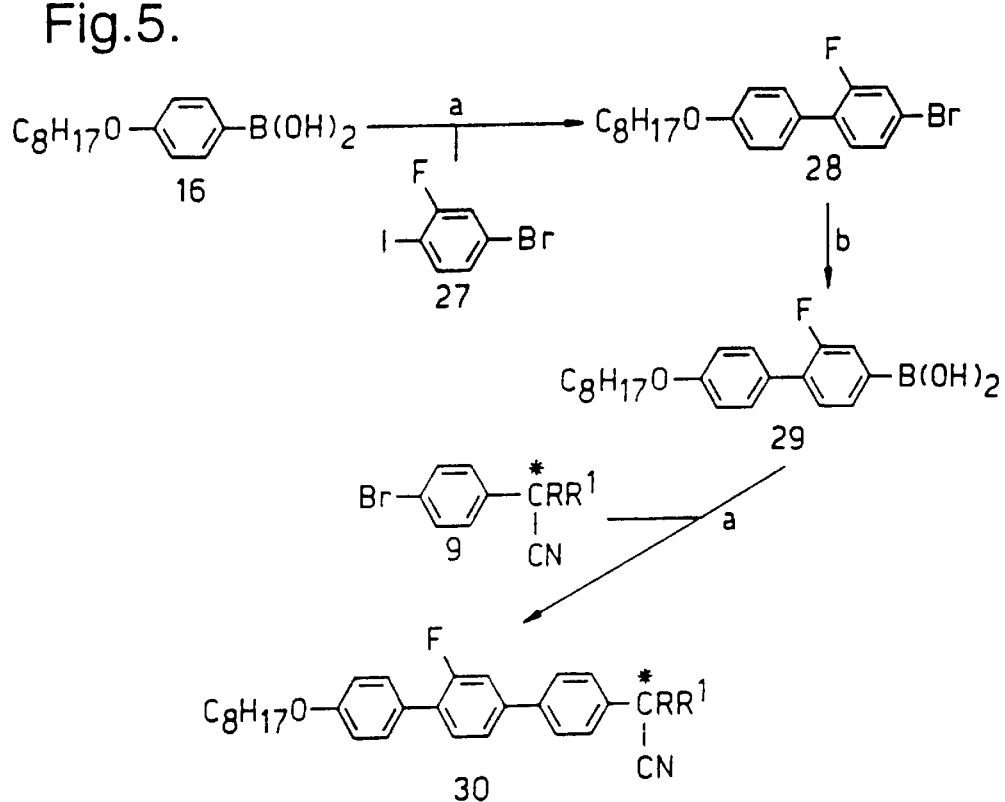
Figure 6:
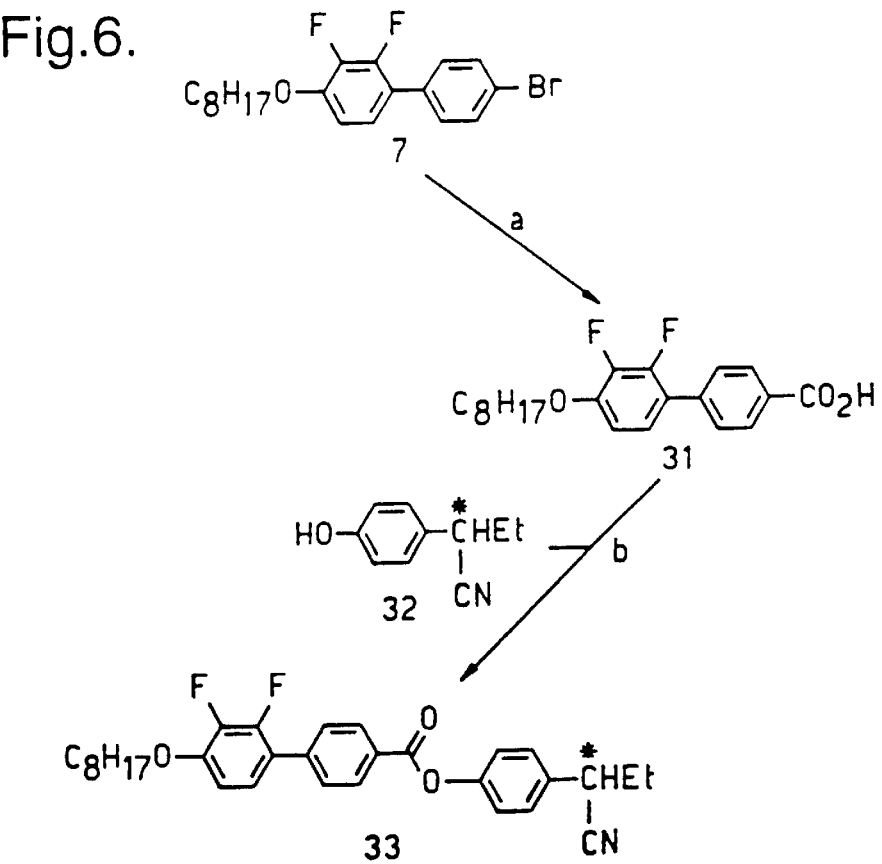
Figure 7:
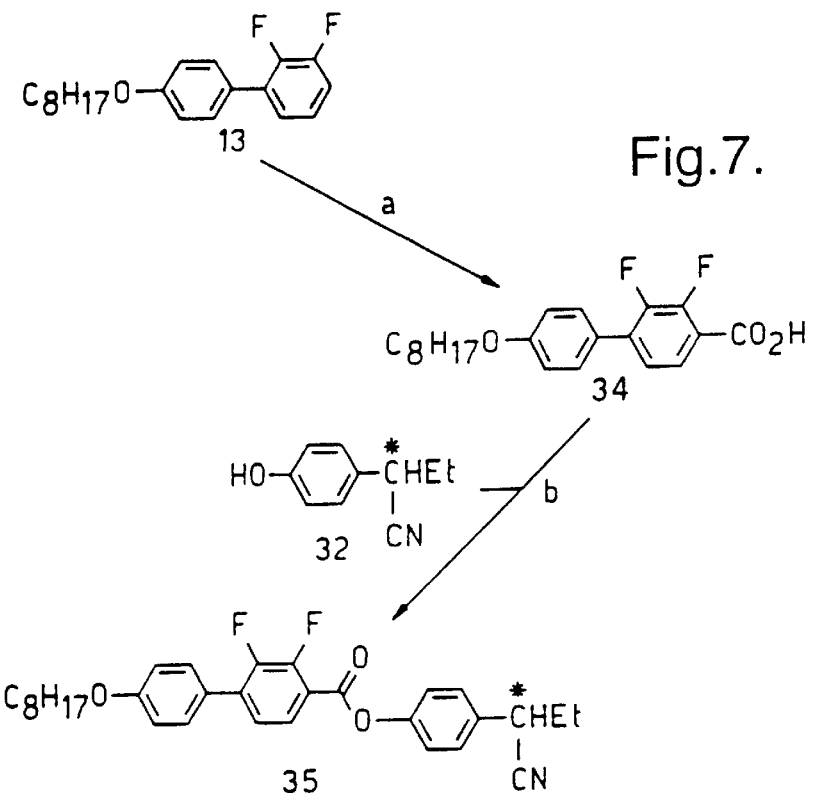
Figure 8:
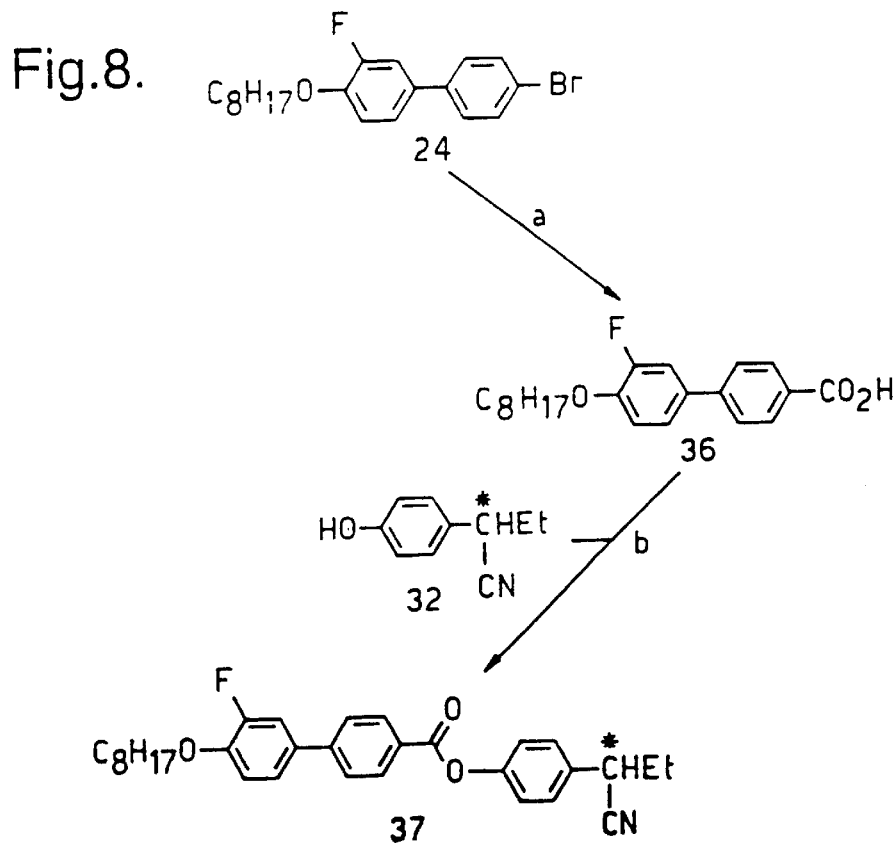
Figure 9:
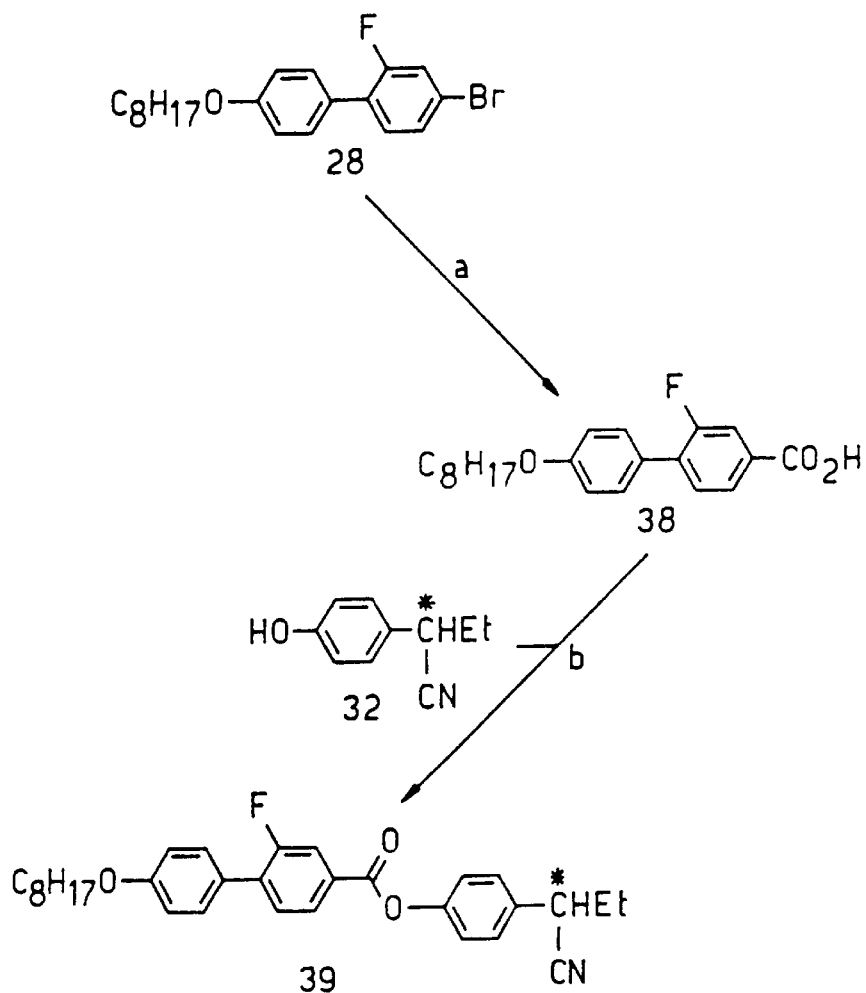

Reagents used in the synthetic routes of FIGS. 1 to 9 are shown below in corresponding schemes 1 to 9.

Scheme 1
a (i) BuLi, THF, (ii) (MeO)$_3$B, THF, (iii) 10% HCl
b $H_2O_2$, THF
c $C_8H_{17}Br$, $K_2CO_3$, butanone
d Pd(PPh$_3$)$_4$, 2M Na$_2$CO$_3$, DME Scheme 2
a $C_8H_{17}Br$, $K_2CO_3$, butanone
b (i) BuLi, THF, (ii) (MeO)$_3$B, THF, (iii) 10% HCl
c Pd(PPh$_3$)$_4$, 2M Na$_2$CO$_3$, DME Scheme 3
a (i) BuLi, THF, (ii) (MeO)$_3$B, THF, (iii) 10% HCl
b Pd(PPh$_3$)$_4$, 2M Na$_2$CO$_3$, DME Scheme 4
a $C_8H_{17}Br$, $K_2CO_3$, butanone
b (i) BuLi, THF, (ii) (MeO)$_3$B, THF, (iii) 10% HCl
c Pd(PPh$_3$)$_4$, 2M Na$_2$CO$_3$, DME Scheme 5
a Pd(PPh$_3$)$_4$, 2M Na$_2$CO$_3$, DME
b (i) BuLi, THF, (ii) (MeO)$_3$B, THF, (iii) 10% HCl Scheme 6
a (i) BuLi, THF, (ii) CO$_2$(s), THF, conc HCl
b DCC, DMAP, DCM Scheme 7
a (i) BuLi, THF, (ii) CO$_2$(s), THF, conc HCl
b DCC, DMAP, DCM Scheme 8
a (i) BuLi, THF, (ii) CO$_2$(s), THF, conc HCl
b DCC, DMAP, DCM Scheme 9
a (i) BuLi, THF, (ii) CO$_2$(s), THF, conc HCl
b DCC, DMAP, DCM

EXPERIMENTAL

Boronic Acid Preparations—Synthesis of Compounds 2, 5, 8, 14, 16, 19, 23, 25 and 29

General Procedure: To a stirred, cooled (−78° C.) solution of the phenyl/biphenyl system in dry tetrahydrofuran, under nitrogen, was added n-butyllithium in a dropwise fashion. This mixture was maintained under these conditions for 2.5 hours or until GC revealed a complete reaction. Trimethylborate in dry tetrahydrofuran was added dropwise and the mixture allowed to warm to room temperature overnight with the cooling bath in place. At room temperature, 10% hydrochloric acid was added and the mixture stirred for 1 hour. The product was then extracted into diethyl ether (×2), washed with water, and dried (MgSO$_4$). After filtration the product was obtained by removing the solvent in vacuo.

Compound 2

| Quantities: | |
|---|---|
| Compound 1 | 15.02 g, 0.132 mol |
| n-Butyllithium, 10M in hexanes | 15.00 ml, 0.150 mol |
| Trimethyl borate | 23.07 g, 0.221 mol |
| Tetrahydrofuran | 180 ml |

Yield—20.19 g (97%) of an off-white waxy solid

Compound 5

| Quantities: | |
|---|---|
| Compound 4 | 2.52 g, 0.010 mol |
| n-Butyllithium, 10M in hexanes | 1.50 ml, 0.015 mol |
| Trimethyl borate | 2.10 g, 0.010 mol |
| Tetrahydrofuran | 90 ml |

Yield—2.43 g (85%) of an pale brown waxy solid

Compound 8

| Quantities: | |
|---|---|
| Compound 7 | 2.76 g, 0.007 mol |
| n-Butyllithium, 1.6M in hexanes | 5.63 ml, 0.009 mol |
| Trimethyl borate | 1.46 g, 0.014 mol |
| Tetrahydrofuran | 100 ml |

Yield—2.29 g (90%) of an off-white waxy solid

Compound 14

| Quantities: | |
|---|---|
| Compound 13 | 5.00 g, 0.016 mol |
| n-Butyllithium, 1.6M in hexanes | 12.5 ml, 0.020 mol |
| Trimethyl borate | 3.13 g, 0.030 mol |
| Tetrahydrofuran | 150 ml |

Yield—6.79 g (112%) of white waxy solid

Compound 16

| Quantities: | |
|---|---|
| Compound 12 | 20.00 g, 0007 mol |
| n-Butyllithium, 10M in hexanes | 10.0 ml, 0.010 mol |
| Trimethyl borate | 14.60 g, 0.014 mol |
| Tetrahydrofuran | 200 ml |

Yield—15.74 g (90%) of an off-white waxy solid

Compound 19

| Quantities: | |
|---|---|
| Compound 18 | 2.49 g, 0.007 mol |
| n-Butyllithium, 2.5M in hexanes | 3.20 ml, 0.008 mol |
| Trimethyl borate | 1.50 g, 0.014 mol |
| Tetrahydrofuran | 100 ml |

Yield—1.91 g (83%) of an off-white waxy solid

Compound 23

| Quantities: | |
|---|---|
| Compound 22 | 10.01 g, 0.033 mol |
| n-Butyllithium, 2.5M in hexanes | 15.00 ml, 0.038 mol |
| Trimethyl borate | 6.86 g, 0.066 mol |
| Tetrahydrofuran | 200 ml |

Yield—7.10 g (79%) a brown waxy solid

Compound 25

| Quantities: | |
|---|---|
| Compound 24 | 3.46 g, 0.0091 mol |
| n-Butyllithium, 2.5M in hexanes | 4.4 ml, 0.0110 mol |
| Trimethyl borate | 1.89 g, 0.0182 mol |
| Tetrahydrofuran | 100 ml |

Yield—2.94 g (93%) a brown waxy solid

Compound 29

| Quantities: | |
|---|---|
| Compound 28 | 4.18 g, 0.011 mol |
| n-Butyllithium, 2.5M in hexanes | 5.2 ml, 0.013 mol |
| Trimethyl borate | 2.70 g, 0.026 mol |
| Tetrahydrofuran | 120 ml |

Yield—3.67 g (96%) a white waxy solid

Conversion of Boronic Acid to Hydroxy Group—Synthesis of Compound 3

General Procedure: Hydrogen Peroxide was added dropwise to a stirred, refluxing solution of boronic acid in tetrahyrofuran. The mixture was refluxed overnight and allowed to cool before being poured into water. The product was extracted into dichloromethane (×2), dried ($MgSO_4$), filtered and obtained after removal of the solvent in vacuo.

Compond 3

| Quantities: | |
|---|---|
| Compound 2 | 23.01 g, 0.15 mol |
| Hydrogen peroxide | 150 ml, 40 vol |
| Tetrahydrofuran | 150 ml |

Yield—18.20 g (93%) of an orange oil.

Alkylation Reactions—Synthesis of Compounds 4, 12 and 22

General Procedure: 1-Bromooctane in butanone was added dropwise to a stirred mixture of the hydroxyphenyl system and potassium carbonate in butanone. The mixture was refluxed until GC revealed a complete reaction and then the mixture was allowed to cool. When cool the potassium carbonate was filtered off and the solvent removed in vacuo. The crude product was distilled to yield a pure product.

Comound 4

| Quantities: | |
|---|---|
| Compound 3 | 1.75 g, 0.013 mol |
| 1-Bromooctane | 3.86 g, 0.020 mol |
| Potassium carbonate | 5.38 g, 0.039 mol |
| Butanone | 65 ml |

Yield—3.10 g (92%) of colourless oil

Comound 12

| Quantities: | |
|---|---|
| Compound 12 | 23.70 g, 0.137 mol |
| 1-Bromooctane | 53.08 g, 0.275 mol |
| Potassium carbonate | 49.06 g, 0.481 mol |
| Butanone | 160 ml |

Yield—35.51 g (91%) of colourless oil

Compound 22

| Quantities: | compound 21 | 19.98 g, 0.104 mol |
| --- | --- | --- |
| | 1-Bromooctane | 24.03 g, 0.124 mol |
| | Potassium carbonate | 28.99 g, 0.210 mol |
| | Butanone | 150 ml |

Yield—24.33 g (80%) of colourless oil

Palladium-Catalysed Cross-coupling Reactions— Synthesis of Compounds 7, 10, 13, 15, 18, 20, 24, 26, 28 and 30

General Procedure: To a stirred solution of the bromo- or iodo-phenyl system in 1,2-dimethoxyethane under nitrogen was sequentially added 2M aqueous sodium carbonate, tetrakis (triphenylphosphine)palladium (O) in dimethoxyethane, and the boronic acid in dimethoxyethane. The mixture was heated overnight at 80–100° C. overnight or until GC revealed a complete reaction. The product was extracted into diethyl ether (×2) and the washed with brine before being dried ($MgSO_4$). The solution was filtered and the product was obtained by removing the solvent in vacuo.
Compound 7

| Quantities: | Compound 5 | 4.55 g, 0.0180 mol |
| --- | --- | --- |
| | 4-Bromo-1-iodobenzene (6) | 4.25 g, 0.0150 mol |
| | Palladium catalyst | 0.58 g, 0.0005 mol |
| | 2M Sodium Carbonate | 100 ml |
| | Dimethoxymethane | 100 ml |

Yield 2.76 g (48%) of white powder after column chromatography with silica gel using 5% dichloromethane in petroleum ether (40–60° C.) as a solvent, and recrystallisation from ethanol.
Compound 10a (R=H, $R^1=C_6H_{13}$)

| Quantities: | Compound 8 | 0.70 g, 0.0019 mol |
| --- | --- | --- |
| | 2-Methyl-2-(4-bromophenyl)octanenitrile (9) | 4.25 g, 0.0016 mol |
| | Palladium catalyst | 0.46 g, 0.0004 mol |
| | 2M Sodium Carbonate | 80 ml |
| | Dimethoxymethane | 80 ml |

Yield 0.51 g (62%) of white powder after column chromatography with silica gel using 10% dichloromethane in petroleum ether (40–60° C.) as a solvent, and recrystallisation from ethanol.
Compound 13

| Quantities: | Compound 2 | 9.10 g, 0.063 mol |
| --- | --- | --- |
| | Compound 12 | 15.31 g, 0.053 mol |
| | Palladium catalyst | 1.44 g, 0.0012 mol |
| | 2M Sodium Carbonate | 200 ml |
| | Dimethoxymethane | 200 ml |

Yield 13.72 (81%) of off-white powder after column chromatography with silica gel using petroleum ether (40–60° C.) as a solvent, and recrystallisation from ethanol.
Compound 15a (R=H. $R^1$=Et)

| Quantities: | Compound 13 | 0.77 g, 0.0021 mol |
| --- | --- | --- |
| | 2-(4-bromophenyl)butyronitrile (9) | 0.34 g, 0.0015 mol |
| | Palladium catalyst | 0.60 g, 0.0005 mol |
| | 2M Sodium Carbonate | 60 ml |
| | Dimethoxymethane | 60 ml |

Yield 0.37 g (36%) of white powder after column chromatography with silica gel using 10% dichloromethane in petroleum ether (40–60° C.) as a solvent, and recrystallisation from ethanol.
Compound 15b (R=Me, $R^1$=Et)

| Quantities: | compound 13 | 0.81 g, 0.0024 mol |
| --- | --- | --- |
| | 2-Methyl-2-(4-bromophenyl)butyronitrile (9) | 0.38 g, 0.0016 mol |
| | Palladium catalyst | 0.70 g, 0.0006 mol |
| | 2M Sodium Carbonate | 60 ml |
| | Dimethoxymethane | 60 ml |

Yield 0.36 g (34%) of white powder after column chromatography with silica gel using 10% dichloromethane in petroleum ether (40–60° C.) as a solvent, and recrystallisation from ethanol.
Compound 18

| Quantities: | Compound 16 | 5.00 g, 0.020 mol |
| --- | --- | --- |
| | 4-Bromo-1-iodobenzene (17) | 4.60 g, 0.015 mol |
| | Palladium catalyst | 0.34 g, 0.0003 mol |
| | 2M Sodium Carbonate | 130 ml |
| | Dimethoxymethane | 130 ml |

Yield 2.53 g (48%) of white crystals after column chromatography with silica gel using 10% dichloromethane in petroleum ether (40–60° C.) as a solvent, and recrystallisation from ethanol.
Compound 20a (R=H, $R^1$=Et)

| Quantities: | Compound 19 | 2.00 g, 0.0055 mol |
| --- | --- | --- |
| | 2-(4-bromophenyl)butyronitrile (9) | 0.83 g, 0.0037 mol |
| | Palladium catalyst | 0.57 g, 0.0005 mol |
| | 2M Sodium Carbonate | 80 ml |
| | Dimethoxymethane | 80 ml |

Yield 0.73 g (41%) of white powder after column chromatography with silica gel using 10% ethyl acetate in petroleum ether (40–60° C.) as a solvent, and recrystallisation from ethanol.
Compound 20b (R=Me, $R^1$=Et)

| Quantities: | Compound 19 | 2.00 g, 0.0055 mol |
| --- | --- | --- |
| | 2-Methyl-2-(4-bromophenyl)butyronitrile (9) | 0.88 g, 0.0037 mol |
| | Palladium catalyst | 0.57 g, 0.0005 mol |
| | 2M Sodium Carbonate | 80 ml |
| | Dimethoxymethane | 80 ml |

Yield 0.93 g (54%) of white powder after column chromatography with silica gel using 20% dichloromethane in petroleum ether (40–60° C.) as a solvent, and recrystallisation from ethanol.

Compound 24

| Quantities: | Compound 23 | 8.31 g, 0.031 mol |
| --- | --- | --- |
| | 4-Bromo-1-iodobenzene (6) | 7.33 g, 0.026 mol |
| | Palladium catalyst | 1.10 g, 0.001 mol |
| | 2M Sodium Carbonate | 80 ml |
| | Dimethoxymethane | 80 ml |

Yield 4.78 g (50%) of white solid after column chromatography with silica gel using petroleum ether (40–60° C.) as a solvent, and recrystallisation from ethanol.

Compound 26 (R=H, $R^1$=Et)

| Quantities: | Compound 25 | 1.00 g, 0.0029 mol |
| --- | --- | --- |
| | 2-(4-bromophenyl)butyronitrile (9) | 0.51 g, 0.0023 mol |
| | Palladium catalyst | 0.11 g, 0.0001 mol |
| | 2M Sodium Carbonate | 60 ml |
| | Dimethoxymethane | 60 ml |

Yield 0.67 g (66%) of white powder after column chromatography with silica gel using 20% ethyl acetate in petroleum ether (40–60° C.) as a solvent, and recrystallisation from ethanol.

Compound 28

| Quantities: | Compound 16 | 3.50 g, 0.014 mol |
| --- | --- | --- |
| | 4-Bromo-1-iodobenzene (27) | 3.44 g, 0.011 mol |
| | Palladium catalyst | 0.42 g, 0.0004 mol |
| | 2M Sodium Carbonate | 60 ml |
| | Dimethoxymethane | 60 ml |

Yield 2.51 g (60%) of while crystals after column chromatography with silica gel using 20% dichloromethane in petroleum ether (40–60° C.) as a solvent, and recrystallisation from ethanol.

Compound 30a (R=H, $R^1$=Et)

| Quantities: | Compound 29 | 1.00 g, 0.0029 mol |
| --- | --- | --- |
| | 2-(4-bromophenyl)butyronitrile (9) | 0.50 g, 0.0022 mol |
| | Palladium catalyst | 0.13 g, 0.0001 mol |
| | 2M Sodium Carbonate | 100 ml |
| | Dimethoxymethane | 100 ml |

Yield 0.45 g (46%) of white powder after column chromatography with silica gel using 20% ethyl acetate in petroleum ether (40–60° C.) as a solvent, and recrystallisation from ethanol.

Compound 30b (R=Me, $R^1$=Et)

| Quantities: | Compound 29 | 1.01 g, 0.0029 mol |
| --- | --- | --- |
| | 2-Methyl-2-(4-bromophenyl)butyronitrile (9) | 0.53 g, 0.0023 mol |
| | Palladium catalyst | 0.13 g, 0.0001 mol |
| | 2M Sodium Carbonate | 100 ml |
| | Dimethoxymethane | 100 ml |

Yield 0.45 g (44%) of white powder after column chromatography with silica gel using 5% dichloromethane in petroleum ether (40–60° C.) as a solvent, and recrystallisation from ethanol.

Compound 30c (R=Me, $R^1$=C_6H_{13}$)

| Quantities: | Compound 29 | 1.01 g, 0.0029 mol |
| --- | --- | --- |
| | 2-Methyl-2-(4-bromophenyl)butyronitrile (9) | 0.67 g, 0.0022 mol |
| | Palladium catalyst | 0.16 g, 0.0001 mol |
| | 2M Sodium Carbonate | 60 ml |
| | Dimethoxymethane | 60 ml |

Yield 0.52 g (44%) of white powder after column chromatography with silica gel using 1:2:7 methanol/dichloromethane/petroleum ether (40–60° C.) as a solvent, and recrystallisation from ethanol.

Formation of Carboxylic Acids—Synthesis of Compounds 31, 34, 36 and 38

General Procedure: n-Butyllithium was added dropwise to a stirred, cooled (−78° C.) mixture of the biphenyl system in dry tetrahydrofuran under nitrogen. The mixture was maintained under these conditions for 2.5 hours or until GC revealed a complete reaction. The mixture was added to a slurry of solid carbon dioxide in dry tetrahydrofuran and allowed to warm to room temperature overnight. When at room temperature the mixture was acidified (conc. HCl) and the product extracted into diethyl ether (×2). The product was obtained after filtration and removal of the solvent in vacuo.

Compound 31

| Quantities: | Compound 7 | 2.30 g, 0.0058 mol |
| --- | --- | --- |
| | n-Butyllithium, 1.6M in hexanes | 4.38 ml, 0.0070 mol |
| | Tetrahydrofuran | 100 ml |
| | Solid carbon dioxide | |

Yield—1.84 g (87%) of white crystals

Compound 34

| Quantities: | Compound 13 | 2.42 g, 0.0061 mol |
| --- | --- | --- |
| | n-Butyllithium, 1.6M in hexanes | 4.56 ml, 0.0073 mol |
| | Tetrahydrofuran | 100 ml |
| | Solid carbon dioxide | |

Yield—2.08 g (94%) of white crystals

Compound 36

| Quantities: | Compound 24 | 3.78 g, 0.0097 mol |
| --- | --- | --- |
| | n-Butyllithium, 1.6M in hexanes | 4.56 ml, 0.0012 mol |
| | Tetrahydrofuran | 100 ml |
| | Solid carbon dioxide | |

Yield—2.89 g (84%) of white crystals

Compound 38

| Quantities: | Compound 28 | 1.89 g, 0.0048 mol |
| --- | --- | --- |
| | n-Butyllithium, 1.6M in hexanes | 3.50 ml, 0.0056 mol |
| | Tetrahydrofuran | 80 ml |
| | Solid carbon dioxide | |

Yield—1.03 g (60%) of white crystals

Esterification Reactions—Synthesis of Compounds 33, 35, 37 and 39

General Procedure: 4-Dimethylaminopyridine in dichloromethane and N,N'-dicyclohexylcarbodimide in dichloromethane were added sequentially to a stirred mixture of the carboxylic acid and the 2,4-hydroxyphenyl-butyronitrilein dichloromethane at room temperature. These conditions were maintained until TLC revealed a complete reaction, the mixture was then filtered, washed with 5% potassium hydroxide and the product extracted into diethyl ether (×2). The mixture was dried (MgSO$_4$) and the product obtained by removal of the solvent in vacuo.

Compound 33

| Quantities: | | |
|---|---|---|
| Compound 31 | 0.99 g, 0.027 mol |
| 4-Hydroxyphenylbutyronitrile (32) | 0.40 g, 0.025 mol |
| N,N'-dicyclohexylcarbodimide | 0.96 g, 00047 mol |
| 4-Dimethylaminopyridine | 0.20 g, 0.0016 mol |
| Dichloromethane | 100 ml |

Yield 0.65 g (52%) of white powder after purification by column chromatography through silica gel in dichloromethane and recrystallisation from ethanol Compound 35

| Quantities: | | |
|---|---|---|
| Compound 34 | 1.03 g, .0029 mol |
| (−)-4-Hydroxyphenylbutyronitrile (32) | 0.41 g, 0.026 mol |
| N,N'-dicyclohexylcarbodimide | 0.61 g, 00050 mol |
| 4-Dimethylaminopyridine | 0.35 g, 0.0017 mol |
| Dichloromethane | 100 ml |

Yield 0.72 g (60%) of white powder after purification by column chromatography through silica gel in dichloromethane and recrystallisation from ethanol Compound 37

| Quantities: | | |
|---|---|---|
| Compound 36 | 0.75 g, .0022 mol |
| 4-Hydroxyphenylbutyronitrile (32) | 0.32 g, 0.0204 mol |
| N,N'-dicyclohexylcarbodimide | 0.54 g, 00026 mol |
| 4-Dimethylaminopyridine | 0.108 g, 0.0089 mol |
| Dichloromethane | 150 ml |

Yield 0.54 g (55%) of white powder after purification by column chromatography through silica gel in dichloromethane and recrystallisation from ethanol Compound 39

| Quantities: | | |
|---|---|---|
| Compound 38 | 0.75 g, .0022 mol |
| (+)-4-Hydroxyphenylbutyronitrile (32) | 0.32 g, 0.0204 mol |
| N,N'-dicyclohexylcarbodimide | 0.54 g, 00026 mol |
| 4-Dimethylaminopyridine | 0.108 g, 0.0089 mol |
| Dichloromethane | 150 ml |

Yield 0.48 g (50%) of white powder after purification by column chromatography through silica gel in dichloromethane and recrystallisation from ethanol Compounds of formula I may be mixed with a wide range of hosts, for example smectic hosts to form a useful liquid crystal composition. Such compositions can have a range of Ps values. Compounds of formula I may be mixed with one or more of the types of hosts VIII–XIII. These different types of hosts may be mixed together to which the compound of general formula I may also be added.

Typical hosts include:

The compounds described in PCT/GB86/00040, e.g. of formula VIII

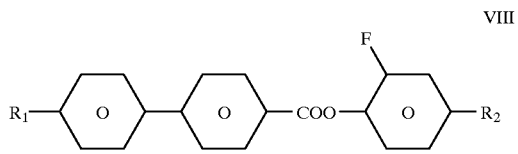

where R$_1$ and R$_2$ are independently C$_3$–C$_{12}$ alkyl or alkoxy.

The fluoro-terphenyls described in EPA 84304894.3 and GBA 8725928, e.g. of formula IX

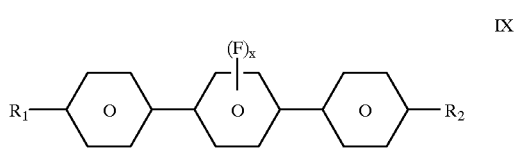

where R$_1$ and R$_2$ are independently C$_3$–C$_{12}$ alkyl or alkoxy, x is 1 and F may be on any of the available substitution positions on the phenyl ring specified.

The difluoro-terphenyls described in GBA 8905422.5, e.g. of formula X

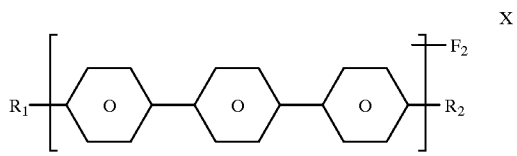

where R$_1$ and R$_2$ are independently C$_3$–C$_{12}$ alkyl or alkoxy.

The phenyl-pyrimidines described in WO 86/00087, e.g. of formula XI

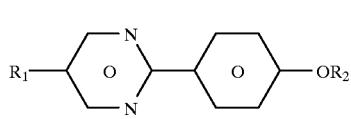

including those compounds where R$_1$ is C$_3$–C$_{12}$ alkyl and R$_2$ is given by the general formula (CH$_2$)$_n$—CHXCH$_2$CH$_3$, where n is 1 to 5 and X is CN or Cl.

The compounds described by R. Eidenschink et. al. in Cyclohexanederivative mit Getilteneten Smektischen Phasen at the 16$^{th}$ Freiberg Liquid Crystal Conference, Freiberg, Germany, p8. Available from E. Merck Ltd., Germany, e.g. of formula XII.

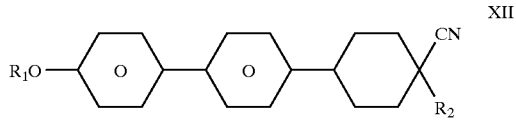

including those compounds where R$_1$ and R$_2$ are independently C$_1$–C$_{15}$ alkyl.

The difluoro-phenyl pyrimidines described in European Patent Application EP 0 332 024 A1, including the following:

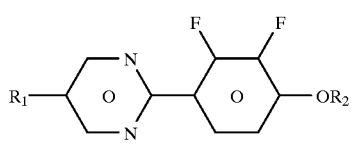
XIII including those compounds where $R_1$ and $R_2$ are independently $C_3$–$C_9$ alkyl.

Figure 10:
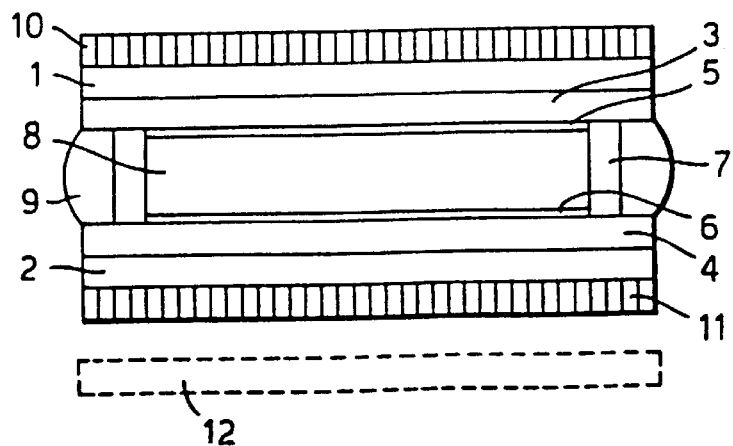
FIG. 10 illustrates a liquid crystal device in which the materials of the current invention may be included.

An example of the use of a compound of Formula I in a liquid crystal material and device embodying the present invention will now be described with reference to FIG. 10.

The liquid crystal device consists of two transparent plates, 1 and 2, in this case made from glass. These plates are coated on their internal face with transparent conducting electrodes 3 and 4. An alignment layer is introduced onto the internal faces of the cell so that a planar orientation of the molecules making up the liquid crystalline material will be approximately parallel to the glass plates 1 and 2. This is done by coating the glass plates 1,2 complete with conducting electrodes 3,4 with layers of film 5 and 6 of a suitable polymer, e.g. polyimide. The electrodes 3,4 may be formed into row and column electrodes so that the intersections between each column and row form an x, y matrix of addressable elements or pixels. Prior to the construction of the cell the films 5,6 are rubbed with a soft tissue in a given direction, the rubbing directions being arranged parallel (same or opposite direction) upon construction of the cell. A spacer 7 e.g. of polymethyl methacrylate separates the glass plates 1 and 2 to a suitable distance e.g. 2 microns. Liquid crystal material 8 is introduced between glass plates 1, 2 by filling the space in between them. The spacer 7 is sealed with an adhesive 9 in a vacuum using an existing technique. Polarisers 10, 11 may be arranged in front of and behind the cell.

The device may operate in a transmissive or reflective mode. In the former, light passing through the device, e.g. from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

Compound 10

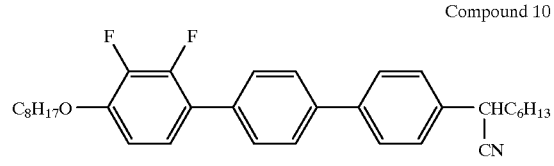

K 105.1 $S_A$ 117.9 I (° C.)

Compound 15

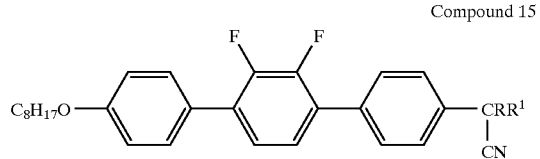

15 a  R = H, $R^1$ = Et   K 98.8 $S_A$ 111.7 I (° C.)
15 b  R = Me, $R^1$ = Et   K 67.8 $S_A$ 69.3 I (° C.)

Compound 20

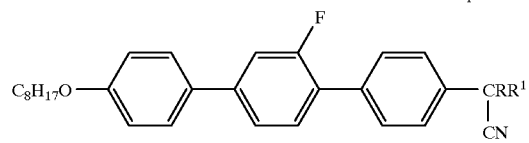

20 a  R = H, $R^1$ = Et   K 92.5 $S_A$ 131.1 I (° C.)
20 b  R = Me, $R^1$ = Et   K 72.1 $S_A$ 80.1 I (° C.)

Compound 26

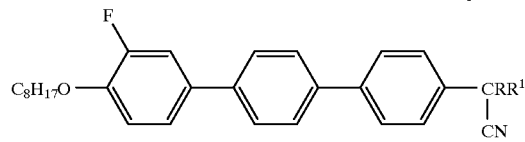

26 a  R = H, $R^1$ = Et   K 97.4 $S_A$ 152.6 I (° C.)

Compound 30

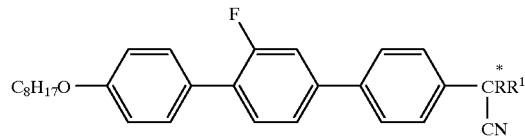

30 a  R = H, $R^1$ = Et   K 63.4 $S_A$ 136.3 I (° C.)
      Optical rotation = -11.73° at 28° C.

30 b  R = Me, $R^1$ = Et   K 53.2 $S_A$ 64.8 I (° C.)
      Optical rotation = -8.73° at 28° C.

30 c  R = Me, $R^1$ = $C_6H_{13}$   K 46.2 $S_A$ 101.2 I (° C.)

Compound 33

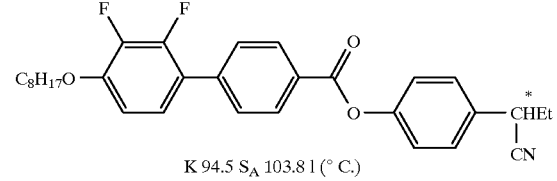

K 94.5 $S_A$ 103.8 I (° C.)

Compound 35

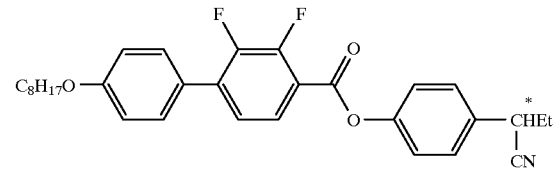

K 98.9 $S_A$ 125.4 I (° C.)
Optical rotation = -9.2° at 22° C.

Compound 37

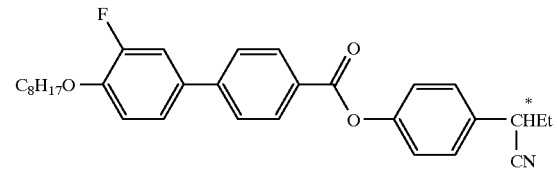

K 98.1 $S_A$ 134.2 I (° C.)

-continued

Compound 39

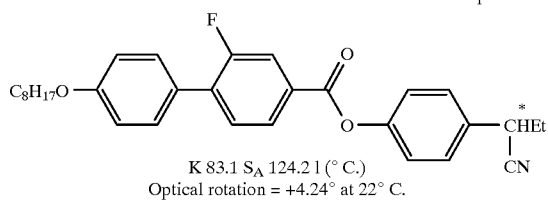

K 83.1 S$_A$ 124.2 I (° C.)
Optical rotation = +4.24° at 22° C.

The compounds of the present invention may be added to host materials.

For example, H1 is a 1:1:1 mixture of the following:

R$_1$=C$_8$H$_{17}$, R$_2$=C$_5$H$_{11}$
R$_1$=OC$_8$H$_{17}$, R$_2$=C$_5$H$_{11}$
R$_1$=OC$_7$H$_{15}$, R$_2$=C$_7$H$_{15}$

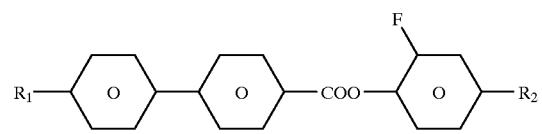

The host is a commercially available host and is widely used in ferroelectric liquid crystal mixtures.

Some of the compounds described by the current invention were mixed with H1 and the effect on the S$_A$ to S$_C$ transition temperature was as follows:

| Dopant | Reduction in S$_A$–S$_C$ transition temp per wt % of dopant added |
|---|---|
| 30a | 1.34 |
| 30b | 2.07 |
| 26a | 1.46 |
| 35 | 2.22 |

The following compound showed a 1.52° reduction of S$_A$–S$_C$ transition temperature per wt % of dopant added:

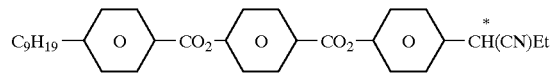

The following compounds were also made according to the present invention:

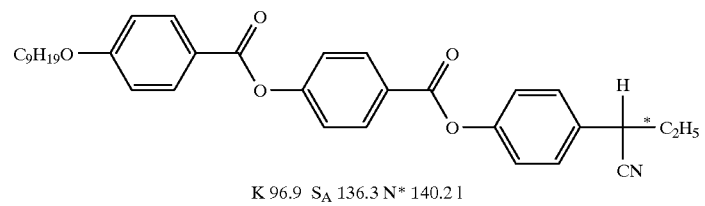

K 96.9 S$_A$ 136.3 N* 140.2 I

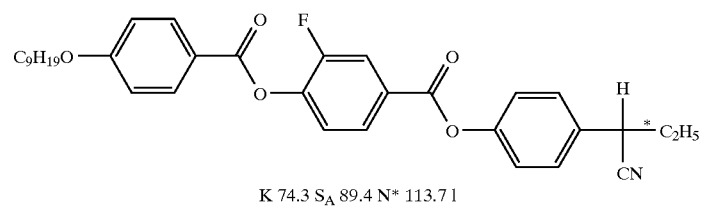

K 74.3 S$_A$ 89.4 N* 113.7 I

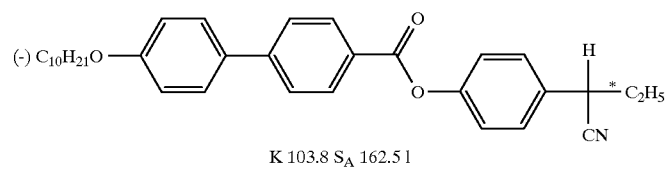

K 103.8 S$_A$ 162.5 I

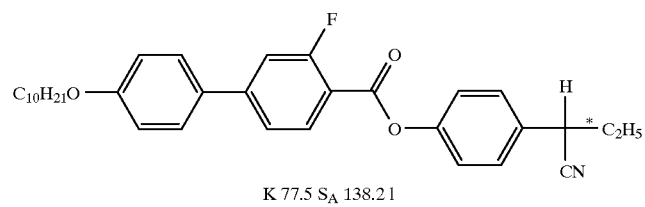

K 77.5 S$_A$ 138.2 I

-continued
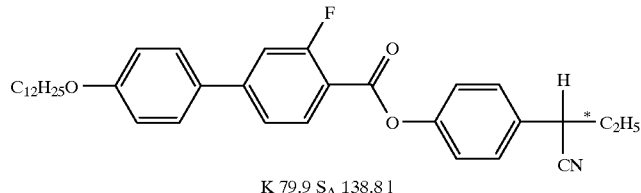
K 79.9 S_A 138.8 I
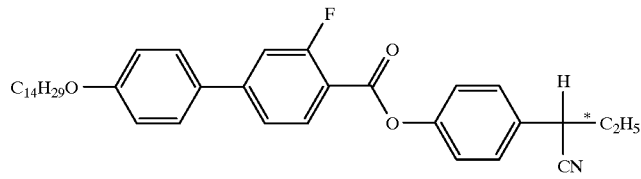
K 81.4 S_A 139.3 I
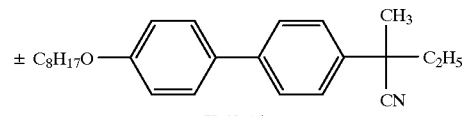
K 62.4 I
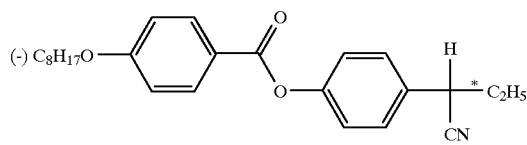
K 63.3 I
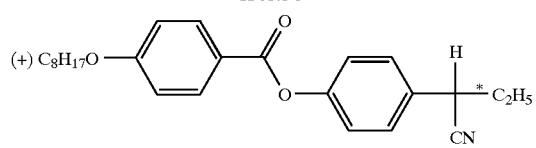
K 65.7 I
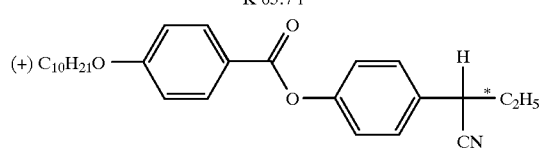
K 78.4 I
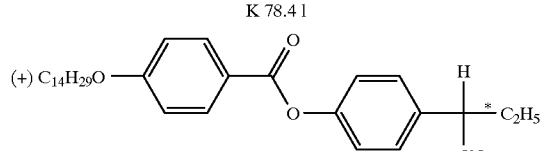
K 81.6 I
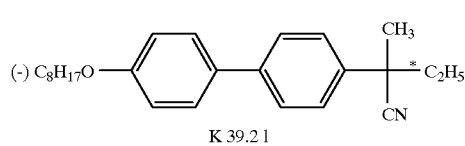
K 39.2 I
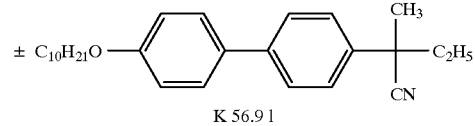
K 56.9 I
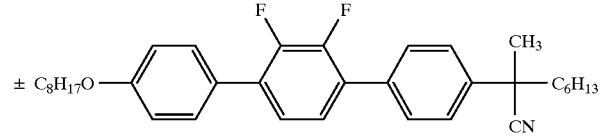
K 105.1 S_A 117.9 I

We claim:
1. A compound having formula I

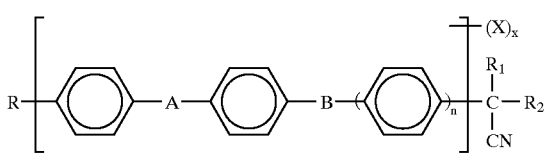

wherein R is $C_{1-16}$ alkyl or alkoxy;
X is selected from F and Cl and indicates that one or more of the phenyl rings is laterally substituted;
x is selected from 1–3;
A and B are independently selected from $CO_2$, OCO, C≡C and single bond;
$R_1$ and $R_2$ are independently selected from H and $C_{1-16}$ straight chain alkyl provided that $R_1$ and $R_2$ are different;
n is 0 or 1 provided that if n is zero then B is a single bond;
provided that when at least one of A and B is $CO_2$ and one of $R_1$ and $R_2$ is H then x is 2 or 3 and one of the substitute phenyl rings bears at least two fluorines.

2. A compound according to claim 1 wherein X is F; A and B are selected from $CO_2$, OCO and single bond; X is F and x is 1 or 2; n is 1.

3. A liquid crystal mixture comprising at least one of the following compounds:

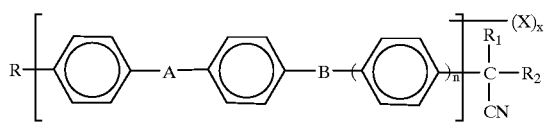

wherein R is $C_{1-16}$ alkyl or alkoxy;
X is selected from F and Cl and indicates that one or more of the phenyl rings may be laterally substituted
x is selected from 0–3;
A and B are independently selected from $CO_2$, OCO, C≡C and single bond
$R_1$ and $R_2$ are independently selected from H and $C_{1-16}$ alkyl provided that $R_1$ and $R_2$ are different;
n is 0 or 1 provided that if n is zero then B is a single bond.

4. A mixture according to claim 3 wherein the mixture is a ferroelectric liquid crystal mixture.

5. A liquid crystal mixture according to claim 3 further comprising a host material of the following general formula:

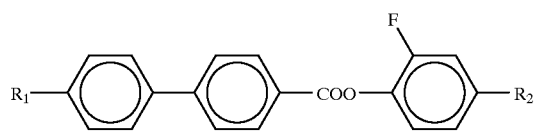

where $R_1$ and $R_2$ are independently $C_3$–$C_{12}$ alkyl or alkoxy.

6. A liquid crystal mixture according to claim 3 further comprising a host material of the following general formula:

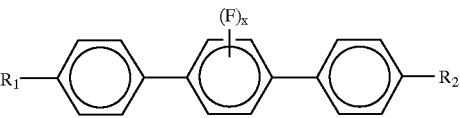

where $R_1$ and $R_2$ are independently $C_3$–$C_{12}$ alkyl or alkoxy, x is 1 and F may be on any one of the available substitution positions on the phenyl ring specified.

7. A liquid crystal mixture according to claim 3 further comprising a host material of the following general formula:

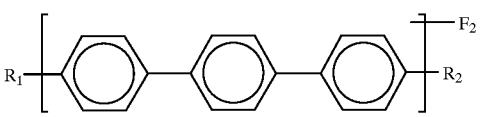

where $R_1$ and $R_2$ are independently $C_3$–$C_{12}$ alkyl or alkoxy.

8. A liquid crystal mixture according to claim 3 further comprising a host material of the following general formula:

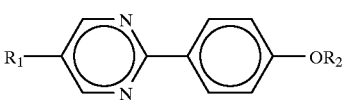

where $R_1$ is $C_3$–$C_{12}$ alkyl and $R_2$ is given by the general formula $(CH_2)_n$—$CHXCH_2CH_3$, where n is 1 to 5 and X is CN or Cl.

9. A liquid crystal mixture according to claim 3 further comprising a host material of the following general formula:

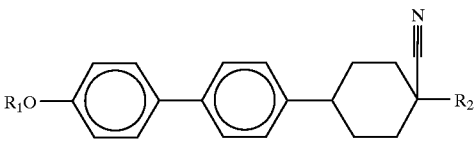

where $R_1$ and $R_2$ are independently $C_1$–$C_{15}$ alkyl or alkoxy.

10. A liquid crystal mixture according to claim 3 further comprising a host material of the following general formula:

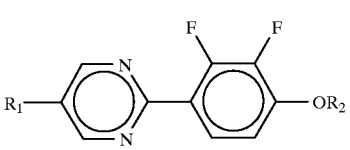

where $R_1$ and $R_2$ are independently $C_3$–$C_9$ alkyl or alkoxy.

* * * * *